US 6,559,120 B2
May 6, 2003

(12) United States Patent
Ball et al.

(10) Patent No.: US 6,559,120 B2
(45) Date of Patent: May 6, 2003

(54) RECOMBINANT ALLERGEN, FRAGMENTS THEREOF, CORRESPONDING RECOMBINANT DNA MOLECULES, VECTORS AND HOSTS CONTAINING THE DNA MOLECULES, DIAGNOSTIC AND THERAPEUTIC USES OF SAID ALLERGENS AND FRAGMENTS

(75) Inventors: Tanja Ball, Vienna (AT); Susanne Vrtala, Vienna (AT); Wolfgang Sperr, Vienna (AT); Peter Valent, Vienna (AT); Markus Susani, Salzburg (AT); Dietrich Kraft, Vienna (AT); Rudolf Valenta, Theresienfeld (AT); Sylvia Laffer, Vienna (AT)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/811,672

(22) Filed: Mar. 20, 2001

(65) Prior Publication Data

US 2002/0052490 A1 May 2, 2002

Related U.S. Application Data

(62) Division of application No. 09/303,684, filed on May 3, 1999, which is a division of application No. 08/750,419, filed as application No. PCT/SE95/00724 on Jun. 14, 1995, now Pat. No. 6,008,340.

(30) Foreign Application Priority Data

Jun. 14, 1994  (SE) ................................................ 9402089

(51) Int. Cl.$^7$ ......................... A61K 38/04; A61K 38/08; A61K 38/10; A61K 38/16
(52) U.S. Cl. .............................. 514/2; 514/12; 514/13; 514/14; 514/15; 514/16
(58) Field of Search ................ 514/2, 12, 13, 514/14, 15, 16

(56) References Cited

U.S. PATENT DOCUMENTS 5,710,126 A    1/1998  Griffith et al.
6,008,340 A  * 12/1999 Ball et al.

FOREIGN PATENT DOCUMENTS

WO    WO9203550     3/1992
WO    WO 9410314    5/1994
WO    WO9421675     9/1994

OTHER PUBLICATIONS

Singh et al., 1999, Int. Arch. Allergy Immunol. 119:75–85.*
Daniel et al., 1994, Virology 202:540–549.*
Freidhoff et al., J. Allergy Clin. Immunol. 78 (1986) 1190–1201.
Laffer et al., J. Allergy Clin. Immunol. 94 (1994) 689–698.
Laffer et al., J. Allergy Clin. Immunol. 94 (1994) 88–94.
Griffith et al., Fed. Eur. Biochem. Soc. 279 (1991) 210–215.
Perez et al., Journal of Biol. Chem. vol. 265, No. 27 (1990) 16210–16215.
George et al., Macromolecular Sequencing and Synthesis, Schlesinger, ed., Alan R. Liss Inc., New York, pp. 127–149 (1998).
Daniel et al., Virology 202:540–549 (1994).
Sambrook et al., Molecular Cloning, Cold Spring Harbor Laboratory Press, Cold Spring Harbor, pp. 9.49–9.51 (1989).
Reeck et al, Cell 50:667 (1987).
Lewin, Science 237:1570 (1987).

* cited by examiner

Primary Examiner—Elizabeth Kemmerer
(74) Attorney, Agent, or Firm—Birch, Stewart, Kolasch & Birch, LLP

(57) ABSTRACT

A recombinant DNA molecule comprising a nucleotide sequence (I) which codes for a polypeptide displaying the antigenicity of one, two or more of the Phi p I epitope clones (28, 34, 41, 42, 43, 45, 50, 52, 64, 80, 85, 86, 95, 97, 98, 103, 108, 109, 113, 114), with the amino acid sequences defined in SEQ ID NOS: 5, 7, 9 and 12–28, and preferably being derived from grasses or monocotyledonic plants, or a nucleotide sequence (II) which hybridizes with such a nucleotide sequence (I) under conditions of high stringency. Polypeptides displaying the antigenicity of one, two or more of the Phi p I epitope clones (28, 34, 41, 42, 43, 50, 52, 64, 80, 85, 86, 95, 97, 98, 103, 108, 109, 113, 114). Recombinant expression vectors containing the recombinant molecule and host cells transformed with the vector. Diagnostic methods based on utilizing the polypeptides in immunoassays for humoral antibodies and cellular reactions.

3 Claims, No Drawings

SEQUENCE LISTING

<160> NUMBER OF SEQ ID NOS: 28

<210> SEQ ID NO 1
<211> LENGTH: 28
<212> TYPE: DNA
<213> ORGANISM: Artificial Sequence
<220> FEATURE:
<223> OTHER INFORMATION: Synthetic oligonucleotide targeted to Timothy
      Grass

<400> SEQUENCE: 1
gggggcttgt ccacatcctt gtacccgc                                          28

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide targeted to Timothy
      Grass

<400> SEQUENCE: 2
ggagaggtcg aagtggtagg gg                                                22

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide targeted to Timothy
      Grass

<400> SEQUENCE: 3
ccgccaccac gtctccgtcg ccg                                               23

<210> SEQ ID NO 4
<211> LENGTH: 63
<212> TYPE: DNA
<213> ORGANISM: Timothy Grass
<220> FEATURE:
<221> NAME/KEY: CDS
<222> LOCATION: (1)..(63)
<223> OTHER INFORMATION:

<400> SEQUENCE: 4 cac atc acc gac gac aac gag gag ccc atc gcc ccc tac cac ttc gac         48
His Ile Thr Asp Asp Asn Glu Glu Pro Ile Ala Pro Tyr His Phe Asp
1               5                   10                  15 ctc tcc ggc cac gcg                                                     63
Leu Ser Gly His Ala
            20

<210> SEQ ID NO 5
<211> LENGTH: 21
<212> TYPE: PRT
<213> ORGANISM: Timothy Grass

<400> SEQUENCE: 5

His Ile Thr Asp Asp Asn Glu Glu Pro Ile Ala Pro Tyr His Phe Asp
1               5                   10                  15

Leu Ser Gly His Ala
            20

<210> SEQ ID NO 6

```
<211> LENGTH: 54
<212> TYPE: DNA
<213> ORGANISM: Timothy Grass
<220> FEATURE:
<221> NAME/KEY: CDS
<222> LOCATION: (1)..(54)
<223> OTHER INFORMATION:

<400> SEQUENCE: 6 aac gag gag ccc atc gcc ccc tac cac ttc gac ctc tcc ggc cac gcg      48
Asn Glu Glu Pro Ile Ala Pro Tyr His Phe Asp Leu Ser Gly His Ala
1               5                   10                  15 ttc ggg                                                              54
Phe Gly

<210> SEQ ID NO 7
<211> LENGTH: 18
<212> TYPE: PRT
<213> ORGANISM: Timothy Grass

<400> SEQUENCE: 7

Asn Glu Glu Pro Ile Ala Pro Tyr His Phe Asp Leu Ser Gly His Ala
1               5                   10                  15

Phe Gly

<210> SEQ ID NO 8
<211> LENGTH: 33
<212> TYPE: DNA
<213> ORGANISM: Timothy Grass
<220> FEATURE:
<221> NAME/KEY: CDS
<222> LOCATION: (1)..(33)
<223> OTHER INFORMATION:

<400> SEQUENCE: 8 gcc ccc tac cac ttc gac ctc tcc ggc cac gcg                          33
Ala Pro Tyr His Phe Asp Leu Ser Gly His Ala
1               5                   10

<210> SEQ ID NO 9
<211> LENGTH: 11
<212> TYPE: PRT
<213> ORGANISM: Timothy Grass

<400> SEQUENCE: 9

Ala Pro Tyr His Phe Asp Leu Ser Gly His Ala
1               5                   10

<210> SEQ ID NO 10
<211> LENGTH: 263
<212> TYPE: PRT
<213> ORGANISM: Timothy Grass

<400> SEQUENCE: 10

Met Ala Ser Ser Ser Val Leu Leu Val Val Leu Phe Ala Val
1               5                   10                  15

Phe Leu Gly Ser Ala Tyr Gly Ile Pro Lys Val Pro Pro Gly Pro Asn
                20                  25                  30

Ile Thr Ala Thr Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
        50                  55                  60

Gly Tyr Lys Asp Val Asp Lys Pro Pro Phe Ser Gly Met Thr Gly Cys
65                  70                  75                  80
```

```
Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Pro Tyr His Phe
            115                 120                 125

Asp Leu Ser Gly His Ala Phe Gly Ala Met Ala Lys Lys Gly Asp Glu
            130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
                180                 185                 190

Asp Gly Asp Val Val Ala Val Asp Ile Lys Glu Lys Gly Lys Asp Lys
                195                 200                 205

Trp Ile Glu Leu Lys Glu Ser Trp Gly Ala Ile Trp Arg Ile Asp Thr
            210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
            260

<210> SEQ ID NO 11
<211> LENGTH: 70
<212> TYPE: PRT
<213> ORGANISM: Timothy Grass

<400> SEQUENCE: 11

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro Lys Asp Asn Gly Gly Ala Cys Gly Tyr Lys Asp Val Asp Lys
            35                  40                  45

Pro Pro Phe Ser Gly Met Thr Gly Cys Gly Asn Thr Pro Ile Phe Lys
        50                  55                  60

Ser Gly Arg Gly Cys Gly
65                  70

<210> SEQ ID NO 12
<211> LENGTH: 43
<212> TYPE: PRT
<213> ORGANISM: Timothy Grass

<400> SEQUENCE: 12

Gly Tyr Lys Asp Val Asp Lys Pro Pro Phe Ser Gly Met Thr Gly Cys
1               5                   10                  15

Gly Asn Thr Pro Ile Phe Lys Ser Gly Arg Gly Cys Gly Ser Cys Phe
            20                  25                  30

Glu Ile Lys Cys Thr Lys Pro Glu Ala Cys Ser
            35                  40

<210> SEQ ID NO 13
```

```
<211> LENGTH: 13
<212> TYPE: PRT
<213> ORGANISM: Timothy Grass

<400> SEQUENCE: 13

Lys Pro Pro Phe Ser Gly Met Thr Gly Cys Gly Asn Thr
1               5                   10

<210> SEQ ID NO 14
<211> LENGTH: 11
<212> TYPE: PRT
<213> ORGANISM: Timothy Grass

<400> SEQUENCE: 14

Pro Val Val Val His Ile Thr Asp Asp Asn Glu
1               5                   10

<210> SEQ ID NO 15
<211> LENGTH: 15
<212> TYPE: PRT
<213> ORGANISM: Timothy Grass

<400> SEQUENCE: 15

His Ile Thr Asp Asp Asn Glu Glu Pro Ile Ala Pro Tyr His Phe
1               5                   10                  15

<210> SEQ ID NO 16
<211> LENGTH: 17
<212> TYPE: PRT
<213> ORGANISM: Timothy Grass

<400> SEQUENCE: 16

Thr Asp Asp Asn Glu Glu Pro Ile Ala Pro Tyr His Phe Asp Leu Ser
1               5                   10                  15

Gly

<210> SEQ ID NO 17
<211> LENGTH: 24
<212> TYPE: PRT
<213> ORGANISM: Timothy Grass

<400> SEQUENCE: 17

Thr Asp Asp Asn Glu Glu Pro Ile Ala Pro Tyr His Phe Asp Leu Ser
1               5                   10                  15

Gly His Ala Phe Gly Ala Met Ala
            20

<210> SEQ ID NO 18
<211> LENGTH: 11
<212> TYPE: PRT
<213> ORGANISM: Timothy Grass

<400> SEQUENCE: 18

Asp Asn Glu Glu Pro Ile Ala Pro Tyr His Phe
1               5                   10

<210> SEQ ID NO 19
<211> LENGTH: 13
<212> TYPE: PRT
<213> ORGANISM: Timothy Grass

<400> SEQUENCE: 19

Glu Pro Ile Ala Pro Tyr His Phe Asp Leu Ser Gly His
1               5                   10
```

<210> SEQ ID NO 20
<211> LENGTH: 27
<212> TYPE: PRT
<213> ORGANISM: Timothy Grass

<400> SEQUENCE: 20

His Val Glu Lys Gly Ser Asn Pro Asn Val Leu Ala Leu Leu Val Lys
1               5                   10                  15

Tyr Val Asn Gly Asp Gly Asp Val Val Ala Val
            20                  25

<210> SEQ ID NO 21
<211> LENGTH: 36
<212> TYPE: PRT
<213> ORGANISM: Timothy Grass

<400> SEQUENCE: 21

Leu Thr Gly Pro Phe Thr Val Arg Tyr Thr Thr Glu Gly Gly Thr Lys
1               5                   10                  15

Thr Glu Ala Glu Asp Val Ile Pro Glu Gly Trp Lys Ala Asp Thr Ser
            20                  25                  30

Tyr Glu Ser Lys
        35

<210> SEQ ID NO 22
<211> LENGTH: 16
<212> TYPE: PRT
<213> ORGANISM: Timothy Grass

<400> SEQUENCE: 22

Gly Pro Phe Thr Val Arg Tyr Thr Thr Glu Gly Gly Thr Lys Thr Glu
1               5                   10                  15

<210> SEQ ID NO 23
<211> LENGTH: 30
<212> TYPE: PRT
<213> ORGANISM: Timothy Grass

<400> SEQUENCE: 23

Val Arg Tyr Thr Thr Glu Gly Gly Thr Lys Thr Glu Ala Glu Asp Val
1               5                   10                  15

Ile Pro Glu Gly Trp Lys Ala Asp Thr Ser Tyr Glu Ser Lys
            20                  25                  30

<210> SEQ ID NO 24
<211> LENGTH: 11
<212> TYPE: PRT
<213> ORGANISM: Timothy Grass

<400> SEQUENCE: 24

Arg Tyr Thr Thr Glu Gly Gly Thr Lys Thr Glu
1               5                   10

<210> SEQ ID NO 25
<211> LENGTH: 29
<212> TYPE: PRT
<213> ORGANISM: Timothy Grass

<400> SEQUENCE: 25

Arg Tyr Thr Thr Glu Gly Gly Thr Lys Thr Glu Ala Glu Asp Val Ile
1               5                   10                  15

```
<210> SEQ ID NO 26
<211> LENGTH: 13
<212> TYPE: PRT
<213> ORGANISM: Timothy Grass

<400> SEQUENCE: 26

Pro Glu Gly Trp Lys Ala Asp Thr Ser Tyr Glu Ser Lys
            20                  25

<210> SEQ ID NO 26
<211> LENGTH: 13
<212> TYPE: PRT
<213> ORGANISM: Timothy Grass

<400> SEQUENCE: 26

Thr Thr Glu Gly Gly Thr Lys Thr Glu Ala Glu Asp Val
1               5                   10

<210> SEQ ID NO 27
<211> LENGTH: 23
<212> TYPE: PRT
<213> ORGANISM: Timothy Grass

<400> SEQUENCE: 27

Gly Thr Lys Thr Glu Ala Glu Asp Val Ile Pro Glu Gly Trp Lys Ala
1               5                   10                  15

Asp Thr Ser Tyr Glu Ser Lys
            20

<210> SEQ ID NO 28
<211> LENGTH: 21
<212> TYPE: PRT
<213> ORGANISM: Timothy Grass

<400> SEQUENCE: 28

Lys Thr Glu Ala Glu Asp Val Ile Pro Glu Gly Trp Lys Ala Asp Thr
1               5                   10                  15

Ser Tyr Glu Ser Lys
            20
```

RECOMBINANT ALLERGEN, FRAGMENTS THEREOF, CORRESPONDING RECOMBINANT DNA MOLECULES, VECTORS AND HOSTS CONTAINING THE DNA MOLECULES, DIAGNOSTIC AND THERAPEUTIC USES OF SAID ALLERGENS AND FRAGMENTS

This application is a divisional of application No. 09/303,684, filed on May 3, 1999, now abandoned, which is a divisional of Application No. 08/750,419, filed on Jan. 14, 1997, now U.S. Pat. No. 6,008,340 which is the national phase of PCT/SE95/00724 filed on Jun. 14, 1995 UNDER 35 U.S.C. §371. The entire contents of each of the above-identified applications are hereby incorporated by reference.

The present invention relates to the title aspects of the major grass pollen allergen Phl p I and IgE-binding epitopes present in this allergen and corresponding haptens. The invention also relates to fragments, including IgE-binding haptens, from other grass and monocotyledonic plant allergens containing the IgE binding epitopes of Phl p I. The invention is primarily concerned with epitopes that normally are found in one or more group I allergens.

BACKGROUND TO THE INVENTION

Up to 20% of the population in industrialized countries suffer from Type I allergic symptoms (rhinitis, conjunctivitis, asthma bronchiale) (Myamoto et al., 1992). The crosslinking of IgE which is bound to mast cells and basophils via the high affinity receptor FcεRI is the key event leading to release of biological mediators such as histamine (Segal et al., 1977). The crosslinking event by allergens represents, therefore, a potential target for therapy of Type I allergy. Such therapeutical approaches could either use portions of the IgE-molecule or other ligands, to interfere with the binding of IgE to the high affinity Fcε-receptor, or reagents to block the subsequent signal transduction cascade thus preventing the degranulation of mast cells and basophils (Dreskin et al., 1988). An additional possibility for specific therapy would be to use haptens derived from complete allergens which by binding to IgE monovalently could block the crosslinking of IgE (Valenta et al., 1993a). IgE-haptens could also be used to modulate the immune response or to induce tolerance by immunotherapy with a minimum of anaphylactic side effects. Haptens can be obtained from complete allergens by proteolytic digestion. However, this often results in a mixture of fragments and enzymes that are difficult to characterize. Synthesis of peptides based on the amino acid sequence of the allergens, is an alternative approach. Recently a number of cDNAs coding for important allergens (Scheiner et al., 1992) were isolated which can be used to determine IgE-epitopes by molecular biological techniques.

Grass pollen allergy is spread world wide and according to the prevalence of grass pollen allergy it can be expected that 75% of all allergic patients suffer from grass pollen allergy (Freidhoff et al., 1986).

Among the grass pollen allergic patients more than 90% display IgE-reactivity with group I allergens (Freidhoff et al., 1986; Valenta et al., 1992).

The full amino acid sequences and nucleotide sequences of the major grass pollen allergens have been known for some time (timothy grass Phl p I (Laffer et al., 1993), rye grass (*Lolium perenne*) Lol p I (Perez et al., 1990; Griffith et al., 1991; University of Melbourne WO-A-9203550,; Brunet C et al., International Symposium on Molecular Biology of Allergens and the Atopic Response, Quebec City, Canada, Feb. 18–22, 1995; Lamontagne P et al., International Symposium on Molecular Biology of Allergens and the Atopic Response, Quebec City, Canada, Feb. 18–22, 1995), and from rye from timothy grass (*Phleum pratense*) Sec c I (Laffer et al., unpublished data).

During the priority year the determination of clones 80, 97 and 98 as carriers for a group I conserved IgE binding epitope has been described (Ball et al., 1994a, b, c; Laffer et al., 1994;).

Definition

The term IgE-hapten identifies short allergen fragments on which only one IgE-antibody with a given specificity is allowed to bind. A real IgE-binding hapten will give no histamine release because it contains the binding site for exclusively one IgE antibody. The term epitope in the context of the present invention refers to an IgE-epitope if not otherwise specified. An epitope may be located on either an IgE-hapten or a longer polypeptide comprising several IgE-binding sites/epitopes. The term IgE preferentially refers to human IgE.

OBJECTIVES OF THE INVENTION

The objectives of the invention are to provide simple, better and more reliable in vitro an in vivo tests for grass pollen allergy as well as improved therapeutic methods for this disease.

The Invention

A first aspect of the invention is a recombinant DNA molecule comprising a nucleotide sequence (I) which codes for a polypeptide displaying the antigenicity of at least one of the Phi p I epitope clones 28 (SEQ ID NO: 26), 34 (SEQ ID NO: 15), 41 (SEQ ID NO: 24), 42 (SEQ ID NO: 27), 43 (SEQ ID NO: 14), 45 (SEQ ID NO: 13), 50 (SEQ ID NO: 18), 52 (SEQ ID NO: 28), 64 (SEQ ID NO: 20), 80 (SEQ ID NO: 5), 85 (SEQ ID NO: 22), 86 (SEQ ID NO: 23), 95 (SEQ ID NO: 17), 97 (SEQ ID NO: 7), 98 (SEQ ID NO: 9), 103 (SEQ ID NO: 19), 108 (SEQ ID NO: 25), 109 (SEQ ID NO: 21), 113 (SEQ ID NO: 12), and 114 (SEQ ID NO: 16) with the amino acid sequences defined in SEQ ID NOS: 5, 7, 9 and 12–28 and preferably being derived from grasses or monocotyledonic plants, or a nucleotide sequence (TI) which hybridizes with a nucleotide sequence (I) under conditions of high stringency. The recombinant DNA molecule comprises also degenerate variants of these nucleotide sequences.

The recombinant DNA molecule may also contain a nucleotide sequence which codes for a polypeptide having antigenic crossreactivity and a high degree of homology, preferable >50% such as >60% or >75%, with Phi p I epitopes from grasses or other monocotyledonic plants, preferably those defined by the amino acid sequences given in SEQ ID NOS: 5, 7 and 9–28.

A second aspect of the invention is a recombinant DNA expression vector or cloning system comprising an expression control sequence operatively linked to any of the recombinant molecules defined above.

A third aspect of the invention is a host cell containing a recombinant molecule or vector according to the first or second aspect, respectively.

A fourth aspect of the invention is a recombinant or synthetic protein or polypeptide displaying the antigenicity of a Phi p I epitope, in particular comprising as an essential part a Phi p I epitope of at least one of the sequences set out in SEQ ID NOS: 5, 7 and 9–28. The protein or polypeptide may be fused to an additional polypeptide, such as β-galactosidase, GST or lambda cII protein or any other polypeptide that can be expressed as a fusion protein in prokaryotic or eukaryotic cells.

In the inventive poly/oligonucleotides and proteins/polypeptides, at least one of the sequences defined in SEQ ID NOS: 5, 7 and 9–28 constitutes an essential part. For the poly/oligonucleotides this means that each of them should not be longer than half of the DNA sequence coding for the full length Phi p I allergen (SEQ ID NO: 10) and preferably containing a nucleotide sequence coding for at least one Phi p I epitope, such as being present in the Phi p I fragments specified in SEQ ID NOS: 5, 7 and 9–28. The inventive oligo/polynucleotides changes are often shorter than 25% of the DNA encoding for the full length phi p I allergen.

For the inventive proteins and polypeptides "essential part" means that each of them should not be longer than half of the full length Phi p I allergen and preferably also contain at least one Phi p I epitope, such as one or more of the epitopes defined by the fragments of the full length Phi p I allergen specified in SEQ ID NOS: 5, 7, 9 and 12–28. The inventive proteins and polypeptides are often shorter than 25% of the full length Phi p I allergen.

By the expression "a polypeptide displaying the antigenicity of at least one of the clones 28, 34, 41, 42, 43, 50, 52, 64, 80, 85, 86, 95, 97, 98, 103, 108, 109, 113, 114" is meant any peptide portion displaying at least one epitope defined by these clones and being recognizable immunologically. It can be envisaged that polypeptides exhibiting Phl p I epitopes may be derivatized to carry analytically detectable groups or water-soluble or water-insoluble solid phases suitable for immunoassays of antibodies directed against them, e.g. IgA, IgD, IgE, IgM or IgG antibodies. In aspects of the invention relating to in vitro diagnostics (see below) the inventive peptides may be a) linked to a water-insoluble phase by physical adsorption or a covalent bond, or b) conjugated covalently to an analytically detectable group (label).

The fifth aspect the invention is an in vitro method for diagnosing allergy to plant proteins by determining humoral antibodies directed towards the plant proteins. The allergies concerned are mostly against grass pollen. The relevant antibodies are mostly of the IgE class but IgG antibodies may also give information about the allergy. In general this method comprises contacting a body fluid sample derived from a patient with an inventive polypeptide. The amounts and conditions are selected so that an immune complex between the polypeptide and antibodies in the sample are formed in an amount that is a function of the amount of antibodies in the sample. The immune complex is then measured in a per se known manner.

More specifically a preferred method of the fifth aspect comprises contacting a body fluid sample containing the Igs concerned, e.g. IgG or IgE, with a polypeptide according to the invention and an anti-IgE antibody so as to form the immune complex containing peptide:IgE:anti-IgE. Normally either the peptide or the anti-IgE is linked to a solid phase that is insoluble or insolubilizable in the assay media so that the complex can be separated from the assay media. The determination step in these variants may be performed by use of an analytically detectable group (label) that either is covalently linked to the anti-IgE antibody (in case the peptide is linked to the solid phase) or to the peptide (in case the anti-IgE antibody is linked to the solid phase). In case IgG antibodies are to be determined anti-IgG replaces anti-IgE.

A sixth aspect of the invention is a method employing measuring, preferably in vitro, the cellular reaction against a Phl p I epitope. The method comprises using a recombinant or synthetic polypeptide as defined for the fourth aspect to stimulate the cellular reaction. Cellular reactions to be measured are histamine release and T cell proliferation (by $^3$H thymidine uptake).

The samples used in the above-mentioned methods are often derived from blood such as whole blood, serum and plasma, although also other body fluids containing Igs may be used (tears etc).

Commonly accepted solid phase forms useful for immunoassays are walls of microtitre wells, spheres, rods, sheets, strips, pads etc. The solid phase may be porous or non-porous. The material in the solid phase may be a polymer selected among polysaccharides and their derivatives, for instance dextran, pullulan, agarose, cellulose etc, or synthetic polymers, preferably vinyl polymers, such as polyacrylamides, polyacrylates, polystyrene, polyvinyl alcohol etc. The polymers in question are often cross-linked, particularly in case the base polymer as such is water-soluble. Examples of analytically detectable groups are isotopes, enzymes, enzyme substrates, fluorophors, haptens, biotin etc.

A seventh aspect of the invention is a method for the treatment of a mammal, such as a human, which has a pollen allergy by administering a therapeutically effective amount of a recombinant or synthetic polypeptide as defined above. Illustrative examples of the therapeutic aspect of the invention are: a) passive therapy of effector organ (nose, conjunctiva, and lung) to prevent mediator release upon subsequent exposition to the complete allergen, and b) use of the peptides as safe tools for active immunotherapy because a single IgE epitope as such do not release mediators so that high doses can be applied. See further in the Discussion part below. The administration routes will be as commonly applied for current hyposensitization. The doses are likely to be in the $\mu$g/ml-range per kg body weight, i.e. 10–100 $\mu$g per kg body weight.

EXPERIMENTAL PROCEDURES

A detailed description referring to the procedure for determining one IgE binding epitope encoded by the clones 80, 97 and 98. During the priority year the same method resulted in that further IgE binding epitopes were deduced (clones 28 (SEQ ID NO: 26), 34 (SEQ ID NO: 15), 41 (SEQ ID NO: 24), 42 (SEQ ID NO: 27), 43 (SEQ ID NO: 14), 45 (SEQ ID NO: 13), 50 (SEQ ID NO: 18), 52 (SEQ ID NO: 28), 64 (SEQ ID NO: 20), 80 (SEQ ID NO: 5), 85 (SEQ ID NO: 22), 86 (SEQ ID NO: 23), 95 (SEQ ID NO: 17), 97 (SEQ ID NO: 7), 98 (SEQ ID NO: 9), 103 (SEQ ID NO: 19), 108 (SEQ ID NO: 25), 109 (SEQ ID NO: 21), 113 (SEQ ID NO: 12), and 114 (SEQ ID NO: 16). See SEQUENCES 2 for their specific sequences and positions within the Phi p I allergen.

Construction of an epitope cDNA library from the randomly fragmented Phl p I cDNA.

The cDNA fragment coding for Phl p I (Valenta et al., 1992; Laffer et al., 1993) was excised from plasmid pUC 18 and purified by preparative agarose gel electrophoresis (Sambrook et al., 1989; Ausubel et al., 1990). The cDNA was then randomly digested with DNAse I (Sambrook et al., 1989; Ausubel et al., 1990) and fragments shorter than 400 bp was isolated by preparative agarose gel electrophoresis. The cDNA fragments were then end repaired with T4 polymerase (Boehringer Mannheim, Germany), linked with 5' phosphorylated 8-mer ECO R I linkers (Schmidheini, Windisch, Switzerland). After Eco R I digestion, linkers were removed using a nick column (Pharmacia Biotech AB, Uppsala, Sweden) and the inserts were ligated into dephosphorylated lambda gt11 arms (Pharmacia Biotech AB, Uppsala, Sweden). The phage DNA was then in vitro packaged using in vitro packaging extracts (Amersham, Buckinghamshire, U.K.). In the recombinant phage particles, the DNA inserts become fused to the gene for β-galactosidase.

IgE-immunoscreening and analysis of epitope clones.

100,000 phages of the Phl p I library were used to infect E. coil Y1090 at a density of 5,000 phages per plate (140 mm diameter). The synthesis of recombinant proteins was induced by overlaying the plates with nitrocellulose filters (Schleicher & Schueli, Dassel, Germany) soaked in 10 mM IPTG (Huynh et al., 1985). 114 Phi p I epitope clones were isolated using serum IgE from a Phi p I allergic patient and 125I labeled rabbit anti-human IgE (Pharmacia Diagnostics, Uppsaia, Sweden) as described (Breiteneder et al., 1989; Valenta et al., 1991; Vrtaia et al., 1993a). The epitope clones were then characterized by hybridization with 3 synthetic oligonucleotides spanning the Phi p I cDNA (Oligo A: 5'GGG GGC TTG TCC ACA TCC TTG TAO CCG C3' bp 191–218, oligo B: 5'GGA GAG GTC GAA GTG GTA GGG G3' bp 372–393, Oligo C: 5'CCG CCA CCA CGT CTC CGT CGC CG3' bp 573–595; SEQ ID NO: 1, SEQ ID NO: 2 and SEQ ID NO: 3, respectively). Nineteen clones that had hybridized with only one of the oligonucleotides were tested for IgE-binding with sera from 12 Phi p I allergic patients. Clones 80 (SEQ ID NO: 5), 97 (SEQ ID NO: 7), and 98 (SEQ ID NO: 9), bound IgE from most patients and were further tested for IgE-reactivity with sera from 90 grass pollen allergic patients as described (Valenta et al., 1992). For DNA sequence analysis, phage DNA was prepared, the epitope encoding cDNAs were excised with KpnI/SacI, suboloned into plasmid pUC 18 and both DNA strands were sequenced using lamba gt11 forward and reversed primers (Clontech, Palo Alto, USA) with $^{35}$S dCTP (Sanger et al., 1977).

Expression and Purification of a Immunodominant Recombinant Phl p I Epitope.

The epitope encoded by clone 98 which bound IgE from 40% of 90 grass pollen allergic patients and contained the shortest cDNA fragment was selected for purification. Recombinant clone 98 phage were used to infect lysogenic E. coli 1089 (Huynh et al., 1985). The Phl p I epitope encoded by clone 93 was expressed as a β-galactosidase fusion protein in liquid culture (Huynh et al., 1985) and was affinity purified using an anti-β-galactosidase affinity column (Promega, Maddison, USA) as described (Vrtala et al., 1993a). β-galactosidase was obtained upon infection of E. coli Y1089 with empty lambda gt11 phage and purified in the same way.

IgE-Binding of Natural Timothy Grass Pollen Allergens and Recombinant Phl p I Epitopes.

Natural timothy grass pollen allergens were extracted from timothy grass pollen (Allergon, Välinge, Sweden) (Vrtala et al., 1993b) separated by SDS-PAGE (Laemmli et al., 1970) and transferred to nitrocellulose (Towbin et al., 1979). The recombinant Phl p I epitope (clone 98) and β-galactosidase were purified and also blotted on nitrocellulose. IgE from grass pollen allergic patients was used to detect the nitrocellulose blotted proteins as described (Jarolim et al., 1989) whereas IgE-binding to non-denatured recombinant epitopes was done using plaquelifts of phage clones as described elsewhere (Spitzauer et al., 1993). IgE-binding synthetic peptides which were prepared by Cambridge Research Biochemicals, U.K. was measured by dot blot assays. One hundred nanograms to two micrograms peptide per spot were dotted to nitrocellulose (Schleicher & Schuell, Dassel, Germany). Reactive peptides derived from other allergens and reactive sera were included as positive controls.

In vitro histamine release from basophils of patients.

Four grass pollen allergic patients with strong IgE-reactivity to group I grass pollen allergens were selected according to case history, serological testing, using RAST and immunoblotting with natural and recombinant grass pollen allergens and skin-prick test as described (Valenta et al., 1992). After informed consent was obtained heparinized blood samples were taken and granulocytes were prepared by dextran sedimentation (Valenta et al., 1989). Granulocytes were then incubated with increasing doses of natural timothy grass pollen allergens, anti-IgE mAb E-124-2-8 (positive control), the recombinant β-galactosidase fused Phl p I (clone 98) epitope and β-galactosidase (negative control), respectively. Liberated histamine expressed as percentage of total histamine was measured in the cell free supernatants by radioimmunoassay (Immunotech, Marseille, France) (Valenta et al., 1989).

To ensure that IgE-antibodies specific for clone 98 were present in the serum of the patient when histamine release was performed, the supernatants which were obtained from the granulocyte preparation were probed in parallel with nitrocellulose blotted timothy grass pollen allergens and the Phl p I (clone 98) epitope as described (Valenta et al., 1993b). The supernatants were from four grass pollen allergic individuals and from a non-allergic control individual. A buffer control without addition of a supernatant was also run.

RESULTS

Isolation and characterization of an immunodominant IgE-epitope clone from Phl p I.

100,000 phages from the Phl p I epitope library were screened using serum IgE from a grass pollen allergic individual with IgE-reactivity to group I grass pollen allergens. 114 IgE-binding phage clones were obtained and subsequently tested for hybridization with 3 synthetic oligonucleotides spanning the Phl p I cDNA. 19 clones which hybridized with only one oligonucleotide were further tested with serum IgE from 12 different Phl p I allergic patients. All tested patients displayed IgE-reactivity with clone 98 which therefore contained an immunodominant epitope. Clone 80 reacted with ten out of twelve Phl p I reactive patients and clone 97 with eleven out of twelve patients. When tested with serum IgE from 90 grass-pollen allergic patients which were selected according to case history, RAST (radioallergosorbent test) and skin prick tests, 40% of the tested sera showed IgE-reactivity with clone 98 whereas 35% reacted with clone 80 and clone 97 (data not shown).

The cDNAS of the three immunodominant epitope clones were sequenced and found to code for almost the same portion of the Phi p I molecule. SEQUENCES 2 (SEQ ID NOS: 5, 7, and 9–28) shows the alignment of the deduced amino acid sequences of the epitope clones with the amino acid sequences of the major grass pollen allergen from timothy grass Phi p I (Laffer et al., 1993). The amino acid of clone 98 was aligned with the amino acid sequences from the other major grass pollen allergens from rye grass (Lolium perenne), Lol p I (Perez et al., 1990; Griffith et al., 1991), and from rye from timothy grass (Phleum pratense), Sec c I (Laffer et al., unpublished data). It was found that Clone 98 (SEQ ID NO: 9) which reacted with IgE from all patients contained a 15 amino acid immunodominant IgE-epitope of Phi p I which is highly conserved among the other group I allergens and covers amino acid 101–115 of the mature Phi p I protein. The C-terminal portion of the peptide seemed to be critical for IgE-binding because clones 80

(SEQ ID NO: 5) and 97 (SEQ ID NO: 7) were less frequently recognized. Peptides of 12 amino acids length were synthesized according to the deduced amino acid sequence of Phl p I with 3 amino acids overlaps, spanning the complete allergen. No reactivity of the patients' IgE with these peptides could be detected indicating that the critical length for IgE-binding of the clone 98 epitope is in the range between 13–15 amino acids (data not shown). Two sythetic peptides (D: aa 76–87, E: aa 117–129) which flanked the clone 98 IgE-epitope also did not bind IgE (data not shown).

Comparison of Different Methods for the Determination of B-Cell Epitopes.

Different methods were used to determine IgE-epitopes (=B-cell epitopes) of Phl p I. Overlapping peptides (Geysen et al., 1987) with a length of 12 amino acids which were synthesized according to the deduced amino acid sequence of Phl p I were tested by dot blotting for reactivity with serum IgE from grass pollen allergic patients. In addition ten peptides covering regions of a predicted high antigenicity (Jameson et al., 1988) of the mature Phl p I allergen:

peptide A: aa 1–17
peptide B: aa 20–39
peptide C: aa 44–69
peptide D: aa 76–87
peptide E: aa 117–129
peptide F: aa 136–147
peptide G: aa 151–159
peptide H: aa 177–193
peptide I: aa 199–209
peptide J: aa 214–237)

were also tested for IgE-reactivity with 35 sera from grass pollen allergic patients by dot blotting. None of the peptides tested reacted with IgE from more than 5% of the grass pollen allergic patients (data not shown).

Since the epitope mapping based on the use of synthetic peptides was unsuccessful, a recombinant mapping strategy was used (Mehra et al., 1986). An epitope expression cDNA library was constructed using randomly fragmented Phl p I cDNA. 114 IgE-epitope clones could be isolated out of 100,000 phages which were screened with IgE from sera of patients. 19 epitope clones containing cDNAs that hybridized only with one oligonucleotide and, therefore, contained small Phl p I fragments were selected. These clones were further tested with sera from 12 different grass pollen allergic patients to determine immunodominant IgE-epitopes. One prominent IgE-epitope encoded by clone 98 was isolated. This sequence was not predicted to be antigenic by computer analysis (Jameson et al., 1988) nor was it identified by testing overlapping synthetic peptides spanning the complete Phl p I molecule (Geysen et al., 1987).

IgE-binding capacity of recombinant Phl p I epitopes.

Recombinant Phl p I epitopes were expressed as β-galactosidase fusion proteins and tested for IgE-binding as native and denatured proteins. β-galactosidase produced by lambda gt11 phage without insert was used as a negative control. Native recombinant IgE-epitopes were obtained by overlaying plates of recombinant E. coli/phage with IPTG soaked membranes (Valenta et al., 1992) whereas for the assays under denaturing conditions, IgE-epitopes were purified by affinity to anti-β-galactosidase antibodies and were separated by denaturing SDS-PAGE (Laemmli et al., 1970) and electroblotted to nitrocellulose (Towbin et al., 1979). Clone 98 bound IgE from all 12 Phl p I allergic patients and when tested with sera from 90 grass pollen allergic patients which were selected according to clinical criteria (case history, RAST and skin prick test) 40% were found reactive.

Although clone 98 represented the immunodominant epitope some clones seemed to possess a higher IgE binding capacity. The denatured immunoblotted clone 98 epitope also bound IgE from group I allergic patients. Compared with natural timothy grass pollen extracts a different intensity of IgE-binding was observed. This may be explained by the presence of group V allergens which comigrate with group I allergens in natural extracts. β-galactosidase did not bind IgE in any of the two assays.

Identification of the immunodominant recombinant Phl p I IgE-epitope (clone 98) as a IgE-hapten by in vitro histamine release assays.

The recombinant Phl p I IgE-epitope encoded by clone 98 was tested for its capacity to release histamine from basophils of grass pollen allergic patients. Although all of the three patients displayed distinct IgE-reactivity to the nitrocellulose blotted recombinant Phl p I epitope, no histamine release was observed when the patients granulocytes were incubated with the purified epitope. A dose dependent and specific histamine release was measured when granulocytes from patients were incubated with natural grass pollen allergens and anti-IgE mAb (positive control) whereas no release was obtained upon incubation with β-galactosidase (negative control). One grass pollen allergic patient 98 epitope but with high levels of IgE against group V allergens was also included in the histamine release assays. This patient showed no histamine release with the clone 98 epitope whereas a dose dependent histamine release could be obtained with total grass pollen extracts that contained group V allergens.

DISCUSSION

The present study demonstrates the efficient determination of IgE-epitopes using recombinant techniques. The cDNA coding for the major grass pollen allergen, Phl p I (Valenta et al., 1992; Laffer et al., 1993), which is the target for IgE-antibodies of 90% of the grass pollen allergic patients, and thus is the target for IgE-antibodies of up to 75% of all allergic patients (Freidhoff et al., 1986; Valenta et al., 1992) was selected as starting material to construct an epitope expression cDNA library. Using IgE of grass pollen allergic patients, an immunodominant IgE-epitope clone containing a Phl p I peptide having a length of 15 amino acids was isolated.

The described 15 amino acids epitope was not predicted by a computer algorithm (Jameson et al., 1988) nor was it detected by overlapping peptide synthesis technology (Geysen et al., 1987).

The knowledge of IgE-epitopes is of particular importance because release of biological mediators such as histamine during the allergic effector reaction requires a divalent cross-link by allergens of IgE bound to mast cells and basophils (Segal et al., 1977). IgE-haptens derived from allergens contain only one IgE-epitope and thus cannot trigger allergic effector mechanisms unless they are polymerized. The immunodominant IgE-epitope which we derived from the major grass pollen allergen Phl p I was therefore purified and tested for its capacity to induce histamine release from the basophils of grass pollen allergic patients. Although in all experiments histamine release could be induced with natural timothy grass pollen allergens in a dose dependent way, no histamine release could be elicited with the recombinant Ph p I epitope which therefore represents an immunodominant IgE-hapten.

IgE-haptens may be useful for two therapeutical approaches of allergic disease: Haptens could be used to block mast cell- and basophil-bound IgE thereby directly inhibiting mediator release. Synthetic epitopes could be synthesized in large amounts and used directly in the effector organs (lung nasal mucosa, conjunctiva) Such an approach would however require the characterization of many different haptens according to the IgE-binding pattern of the patient. Using recombinant DNA techniques for the characterization of allergens and the determination of IgE-epitopes such an approach may be feasible. In addition, it is expected that due to extensive immunological crossreactivities among most allergens it might be possible to define a limited number of IgE-epitopes (Valenta et al., 1993a). As was demonstrated for Phl p I, IgE-epitopes can be determined by immunoscreening of expression libraries derived from cDNAs of allergens. A representative number of patients can then be tested for IgE-reactivity with recombinant epitope clones to obtain immunodominant structures. In a second step most of the additional relevant IgE-epitopes of each allergen have to be characterized. This might be possible because B-cell epitopes, unlike T-cell epitopes, assemble a larger conformation that also has to be available on the surface of the allergen (Berzofsky et al., 1985; Chothia et al., 1991; Laver et al., 1990). thus it can be assumed that the diversity of B-cell epitopes may be much more restricted than that of T-cell epitopes.

In addition to the blocking of the allergic effector reaction, IgE-haptens could also be used to modulate IgE-responses by applying vaccination strategies which aim at the induction of immunological tolerance. Hyposensitization treatment of Type I allergies which is established world wide requires the increasing application of allergens by injection or oral administration. Although hyposensitizations is used successfully since 1911 (Noon et al., 1911), many patients undergoing this therapy suffer from severe side effects such as anaphylactic shock. The use of IgE-haptens derived from the allergens might contribute considerably to the improvement of this therapy by reduction of such side effects. Different other methods to modulate the IgE-response in allergic patients which are currently developed might also take advantage from the use of IgE-haptens.

In conclusion our study demonstrates that by use of recombinant techniques an immunodominant IgE-hapten from the major timothy grass pollen allergen Phl p I could be obtained. This allergen was selected as a model allergen because a high proportion (>90%) of all grass pollen allergic patients, and thus almost 75% of all allergic patients show IgE-reactivity with this molecule. Although the obtained 10 amino acids epitope bound IgE from approximately 40% of grass pollen allergic patients, it did not release histamine from the basophils of patients and may therefore be considered as a hapten. We are aware that in addition to the described Phl p I epitope certainly more epitopes from the same molecule and other allergens must be defined to block histamine release by saturating mast cells and basophils of allergic patients. However, the results encourage to continue with the characterization of IgE-haptens for their future use in specific therapy of allergic diseases.

REFERENCES

1. Ausubel F M, In: Current protocols in Molecular Biology, Wiley, New York (1990)
2. Ball T et al., J. Biol. Chem. 269 (1994) 28323–28328
3. Ball et al., XV Annual Meeting of the European Academy of Allergology and Clincal Immunology, Stockholm, Sweden, Jun. 26-Jul. 1, 1994
4. Ball et al., 12th European Immunology Meeting, Barcelona, Spain, Jun. 14–17, 1994
5. Brunet C et al., International Symposium on Molecular Biology of Allergens and the Atopic Response, Quebec City, Canada, Feb. 18–22, 1995
6. Berzofsky J A, Science 229 (1985) 923–940
7. Breiteneder H et al., EMBO J. 8 (1989) 1935–1938
8. Chothia C, Current Opinion in Structural Biology 1 (1991) 53–59
9. Dreskin S C et al., J. Am. Med. Ass. 260 (1988) 1265–1268
10. Freidhoff L R et al., J. Allergy Clin. Immunol. 78 (1986) 1190–1201
11. Geysen H M et al., J. Immunol. Meth. 102 (1987) 259–274
12. Griffith I J et al., FEBS lett. 279 (1991) 210–215
13. Huynh T V et al., In: cDNA cloning, Oxford, IRL Press, 1 (1985) 49–78
14. Jameson B A et al., CABIOS 4 (1988) 181–186
15. Jarolim E et al., Allergy 44 (1989) 385–395
16. Laemmli U K, Nature (Lond.) 227 (1970) 680–685
17. Laffer S et al., J. Allergy Clin. Immunol (1993 in press)
18. Laffer et al., 12th European Immunology Meeting, Barcelona, Spain, Jun. 14–17, 1994
19. Lamontagne P et al., International Symposium on Molecular Biology of Allergens and the Atopic Response, Quebec City, Canada, Feb. 18–22, 1995
20. Laver W G et al., Cell 61 (1990) 553–556
21. Mehra V et al., Proc. Natl. Acad. Sci. USA 83 (1986) 7013–7017
22. Miyamoto T, In: Advances in Allergology and Clinical Immunology, Eds Godard P et al., The Parthenon Publishing Group-Carnforth, U.K. and New Jersey, USA, (1992) 343–347
23. Noon L, Lancet 1 (1911) 1572
24. Perez M et al., J. Biol. Chem. 265 (1990) 16210–16215
25. Sambrook J et al., In: Molecular cloning: A laboratory manual, Cold Spring Harbor Laboratory Press (1989)
26. Sanger F et al., Proc. Natl. Acad. Sci. USA 74 (1977) 5463–5468
27. Ferreira et al., In: Advances in Allergology and Clinical Immunlogy, Eds. Godard P et al., The Parthenon Publishing Group-Carnforth, U.K. and New Jersey, USA, (1992) 115–126
28. Segal D M et al., Proc. Natl. Acad. Sci. USA 41 (1977) 457–467
29. Spitzauer S et al., J. Allergy Clin. Immunol. (1993 in press???)
30. Towbin H et al., Proc. Natl. Acad. Sci. USA 76 (1979) 4350–4354
31. Valent P et al., Proc. Natl. Acad. Sci. USA 86 (1989) 5542–5546
32. Valenta R et al., Science 253 (1991) 557–560
33. Valenta R et al., Int. Arch. Allergy Appl. Immunol. 97 (1992) 287–294
34. Valenta R et al., In: Vaccines 93, Eds Ginsberg H S et al., Cold Spring Harbor Laboratory Press, New York, USA (1993a) 37–41
35. Valenta R et al., J. Allergy Clin. Immunol. 91 (1993b)
36. Vrtala S et al., J. Immunol. 151 (1993a) 4773–4781
37. Vrtala S et al., Int. Arch. Allergy Immunol 102 (1993b) 160–169
38. University of Melbourne (WO-A-9203550)

SEQUENCES 1. cDNA and deduced amino acid sequence of Phi p I epitope clones discovered up to the priority date (c80 (SEQ ID NOS: 4 and 5), c97 (SEQ ID NOS: 6 and 7) c98 (SEQ ID NOS: 8 and 9)).

```
c80: CAC ATC ACC GAC GAC AAC GAG GAG CCC ATC GCC CCC TAC CAC TTC
      H   I   T   D   D   N   E   E   P   I   A   P   Y   H   F

GAC CTC TCC GGC CAC GCG
      D   L   S   G   H   A

C97: AAC GAG GAG CCC ATC GCC CCC TAC CAC TTC GAC CTC TCC GGC CAC
      N   E   E   P   I   A   P   Y   H   F   D   L   S   G   H

GCG TTC GGG
      A   F   G

C98: GCC CCC TAC CAC TTC GAC CTC TCC GGC CAC GCG
      A   P   Y   H   F   D   L   S   G   H   A
```

SEQUENCES 2. Alignment of the deduced amino acid sequences of all Phi p I IgE-epitope clones (SEQ ID NOS: 5, 7, 9 and 12–28) with the full amino acid sequence of the Phi p I allergen (SEQ ID NO: 10).

The clone number is at the right end. The full amino acid sequence of the Phl p I allergen is given by the longest lines (SEQ ID NO: 10). The underlined part corresponds to the signal peptide and is not present in the mature polypeptide.

```
MASSSVLLVVLFAVFLGSAYGIPKVPPPGPNITATYGDKWDAKSTWYGKPTG
AGPKDNGGAC       GIPKVPPPGPNITATYGDKWDAKSTWYGKPTG
AGPKDNGGAC   GYKDVDDKPPFSGMTGCCGNTPIFKSGRGCGSCFEIKCTKPEACSG
             GYKDVDDKPPFSGMTGCCGNTPIFKSGRGCG           NT
             GYKD KPPFSGMTGCCGNTPIFKSGRGCGSCFEIKCTKPEACS 113
EPVVVHITDDNEEPIAPYHFDLSGHAFGAMAKKGDEQKLRSAGELQFRRVKC
 PVVV HITDDNEEPIAPYHFDLSGHA  80
           43
            NEEPIAPYHFDLSGH  114
            NEEPIAPYHFDLSGHAFGAMA 95
         TD NEEPIAPYHFDLSGHAFG 97
             NE EPIAPYHFDLSGHAFGAM 98

KYPEGTKVTFHVEKGSNPNYLALLVKKYVNGDGDVVAVDIKEKGKDKWIELKESW
                  HVLHVEKGSNPNVLATEEGGTKTEADVIPEGWKADTSYESK
GAIWRIDTPDKLTGPFTVRYTTEGGTKTEAEDVIPEGWKADTSYESK 109
          LTGPFTVRYTTEGGTKTEAEDV  28 IPEGWKADTSYESK 86
             VRYTTEGGTKTEAEDVIPEGWKADTSYESK 108
                41
              RYTTEGGTKTEAEDVIPEGWKADTSYESK 42
               TTEGGTKKTEAEDVIPEGWKADTSYESK 52
                    GTKKTEAEDV                  85
                                                64
                                                50
                                                45
                                                34
                                               103
```

What is claimed is:

1. A method of treatment of an animal which has a pollen allergy which comprises administering a therapeutically effective amount of a recombinant or synthetic protein or polypeptide comprising at least one of the Phl p I epitopes defined by the amino acid sequences given in clones 28 (SEQ ID NO: 26), 34 (SEQ ID NO: 15), 41 (SEQ ID NO: 24), 42 (SEQ ID NO: 27), 43 (SEQ ID NO: 14), 45 (SEQ ID NO: 13), 50 (SEQ ID NO: 18), 52 (SEQ ID NO: 28), 64 (SEQ ID NO: 20), 80 (SEQ ID NO: 5), 85 (SEQ ID NO: 22), 86 (SEQ ID NO: 23), 95 (SEQ ID NO: 17), 97 (SEQ ID NO: 7), 98 (SEQ ID NO: 9), 103 (SEQ ID NO: 19), 108 (SEQ ID NO: 25), 109 (SEQ ID NO: 21), 113 (SEQ ID NO: 12), and 114 (SEQ ID NO: 16).

2. The method of claim 1 wherein the protein or polypeptide is fused to an additional polypeptide.

3. The method of claim 2 wherein said additional polypeptide is β-galactosidase, GST or lambda cII protein or any other polypeptide that can be expressed as a fission protein in prokaryotic or eukaryotic cells.

* * * * *

UNITED STATES PATENT AND TRADEMARK OFFICE
CERTIFICATE OF CORRECTION

PATENT NO.     : 6,559,120 B2
DATED          : May 6, 2003
INVENTOR(S)    : Tanja Ball et al.

Page 1 of 1

It is certified that error appears in the above-identified patent and that said Letters Patent is hereby corrected as shown below:

Column 26,
Line 46, change "fission" to -- fusion --.

Signed and Sealed this

Twenty-eighth Day of June, 2005

JON W. DUDAS
*Director of the United States Patent and Trademark Office*